(12) United States Patent
Elf et al.

(10) Patent No.: US 10,570,437 B2
(45) Date of Patent: *Feb. 25, 2020

(54) PHENOTYPIC CHARACTERIZATION AND IN SITU GENOTYPING OF A LIBRARY OF GENETICALLY DIFFERENT CELLS

(71) Applicant: Astrego Diagnostics AB, Uppsala (SE)

(72) Inventors: Johan Elf, Uppsala (SE); Ove Öhman, Uppsala (SE); George Church, Brookline, MA (US)

(73) Assignee: ASTREGO DIAGNOSTICS AB, Uppsala (SE)

( * ) Notice: Subject to any disclaimer, the term of this patent is extended or adjusted under 35 U.S.C. 154(b) by 291 days.

This patent is subject to a terminal disclaimer.

(21) Appl. No.: 15/323,352

(22) PCT Filed: Feb. 27, 2015

(86) PCT No.: PCT/SE2015/050227
§ 371 (c)(1),
(2) Date: Dec. 30, 2016

(87) PCT Pub. No.: WO2016/007063
PCT Pub. Date: Jan. 14, 2016

(65) Prior Publication Data
US 2017/0159048 A1  Jun. 8, 2017

(30) Foreign Application Priority Data

Jul. 7, 2014  (SE) ..................... 1450860

(51) Int. Cl.
| | | |
|---|---|---|
| *C12Q 1/18* | (2006.01) | |
| *C12Q 1/6874* | (2018.01) | |
| *C12N 15/10* | (2006.01) | |
| *C12Q 1/6806* | (2018.01) | |
| *G01N 33/483* | (2006.01) | |
| *B01L 3/00* | (2006.01) | |
| *C12Q 1/6841* | (2018.01) | |

(52) U.S. Cl.
CPC .......... *C12Q 1/18* (2013.01); *B01L 3/502761* (2013.01); *C12N 15/1093* (2013.01); *C12Q 1/6806* (2013.01); *C12Q 1/6841* (2013.01); *C12Q 1/6874* (2013.01); *G01N 33/4833* (2013.01)

(58) Field of Classification Search
CPC ............ C12Q 1/18; B01L 3/502761
USPC ........................................ 506/10
See application file for complete search history.

(56) References Cited

U.S. PATENT DOCUMENTS

2011/0212440 A1  9/2011  Viovy et al.
2013/0115606 A1  5/2013  Hansen et al.

FOREIGN PATENT DOCUMENTS

| WO | 2009/021215 A1 | 2/2009 |
|---|---|---|
| WO | 2012/106546 A2 | 8/2012 |
| WO | 2013/130714 A1 | 9/2013 |
| WO | 2013/169917 A1 | 11/2013 |
| WO | 2014/005042 A2 | 1/2014 |
| WO | 2014/093118 A1 | 6/2014 |

OTHER PUBLICATIONS

Laufer et al., Mapping genetic interactions in human cancer cells with RNRNAi and multiparametric phenotyping, Nature Methods, vol. 10, No. 5, pp. 427-433 (May 2013).
Lawson et al., In situ genotyping of a pooled strain library after characterizing complex phenotypes, Molecular Systems Biology, 13:947, pp. 1-9 (online Oct. 17, 2017).
Zhicheng Long et al., Microfluidic chemostat for measuring single cell dynamics in bacteria, Lab Chip, 13:947-954 (2013).
Je Hyuk Lee et al., Highly Multiplexed Subcellular RNA Sequencing in Situ, Science, 343:1360-1364 (online Feb. 27, 2014).
Nawy, Sequencing, The big RNA picture, Nature Methods, 11(5):471 (May 2014).
Diego Adhemar Jaitin et al., Massively Parallel Single-Cell RNA-Seq for Marker-Free Decomposition of Tissues into Cell Types, Science, 343:776-780 (Feb. 14, 2014).
Diego Adhemar Jaitin et al., Supplementary Material for Massively Parallel Single-Cell RNA-Seq for Marker-Free Decomposition of Tissues into Cell Types, Science, 343(776):1-35 (Feb. 14, 2014).
Liang Zhu et al., Filter-based microlluidic device as a platform for immunofluoriescent assay of microbial cells, Lab Chip, 4:337-341 (2004).
English Translation of Official Action dated Apr. 2, 2019 from corresponding Japanese Patent Application No. 2017-501162.

*Primary Examiner* — Karla A Dines
(74) *Attorney, Agent, or Firm* — Porter Wright Morris & Arthur LLP

(57) ABSTRACT

A library of cell strains is characterized by culturing cells at spatially defined and separated positions in a culturing device (1) and determining a phenotypic characteristic of each cell strain in the culturing device (1). The cells are fixated at the spatially defined and separated positions in the culturing device (1) followed by in situgenotyping a respective variable region (150) of each cell strain at the spatially defined and separated positions in the culturing device (1). Each respective phenotypic characteristic is connected to each respective genotype based on the spatially defined and separated positions in the culturing device (1).

28 Claims, 8 Drawing Sheets

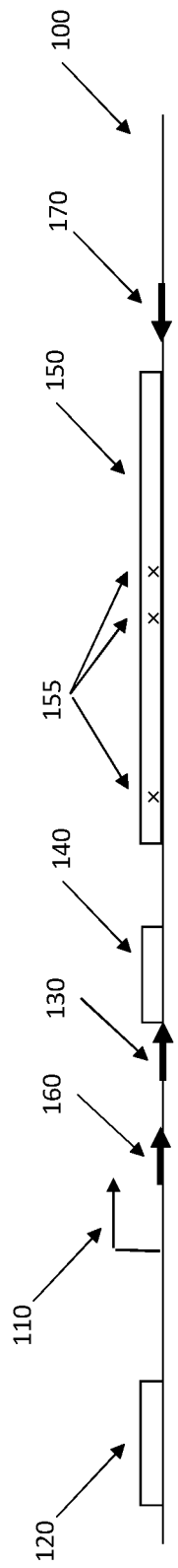
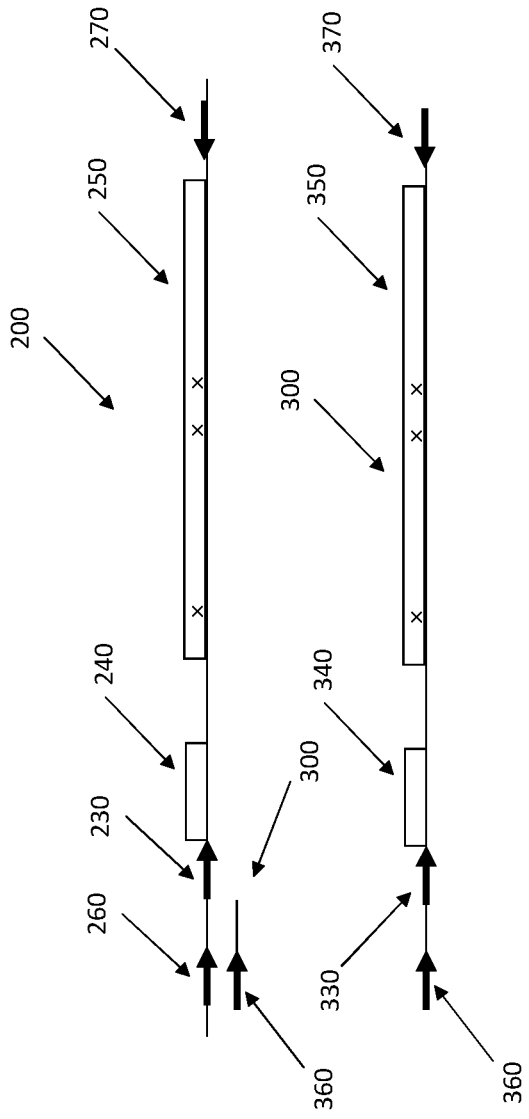
Fig. 8
Fig. 9
Fig. 10

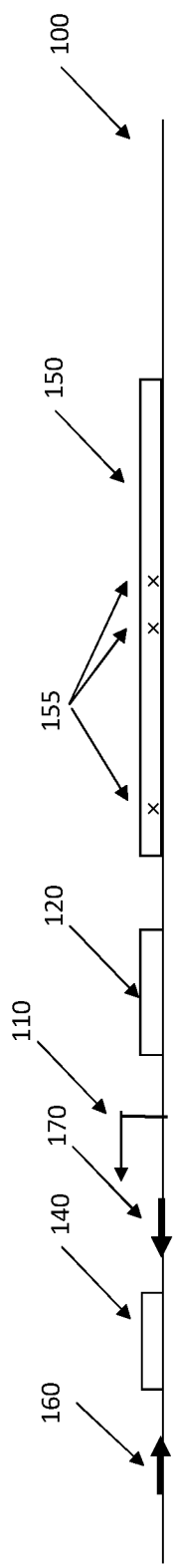
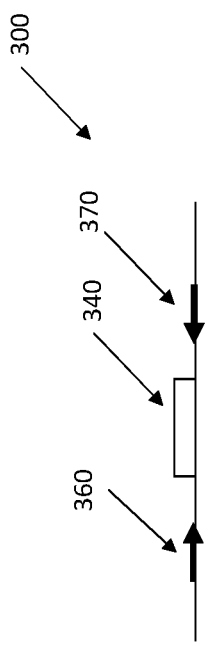

PHENOTYPIC CHARACTERIZATION AND IN SITU GENOTYPING OF A LIBRARY OF GENETICALLY DIFFERENT CELLS

TECHNICAL FIELD

The present embodiments generally relate to phenotypic characterization and in situ genotyping of a library of genetically different cells.

BACKGROUND

The recent development in genome engineering, for instance exemplified by Multiplex Automated Genomic Engineering (MAGE) and applications of Clustered Regularly Interspaced Short Palindromic Repeats (CRISPR) associated protein 9 (Cas9) or other types of genome editing facilitated by engineered nucleases, such as Zinc finger nucleases (ZFNs) and Transcription Activator-Like Effector Nucleases (TALENs), in combination with decreased costs for DNA oligonucleotide synthesis, makes it possible to generate large cell libraries with overwhelming genetic diversity. At the same time technology development has led to the possibility of determining phenotypic and genotypic characteristics of cells. For instance, Fluidigm Dynamic Array™ integrated fluidic circuits (IFC) can be used for genotyping in a single microwell plate. However, the size of the cell libraries that can be analyzed is restricted to a few hundred different cells since the genetically different cells must be kept sorted and analyzed individually.

Another technology that can handle significantly larger strain libraries than Fluidigm Dynamic Array™ IFC is fluorescence-activated cell sorting (FACS). However, FACS has limitations since the phenotypic characterization of the cell libraries is limited to fluorescence readout at a single point in time. In vitro compartmentalization (IVC) and droplet-based technology can, similar to FACS, handle large libraries. However, the phenotypic information obtained in IVC is limited because of optical constraints for imaging in droplets and by the fact that long term cell growth experiments cannot be performed in the droplets.

Yet other techniques depend on adding barcoded oligomers to cells after imaging. The need for distribution of oligomers to specific spatial positions limits the conditions under which cells can be grown and the number of different barcodes that can be distributed.

Thus, there is a need for improvements within the technical field of phenotypic and genotypic characterization of cell libraries. In particular, there is a need for a technology that can handle large cell libraries and that can monitor phenotypic characteristics with high spatial and temporal resolution.

SUMMARY

It is a general objective to provide a technology that allows phenotypic and genotypic characterization of large cell libraries.

This and other objectives are met by embodiments as defined herein.

Briefly, an aspect of the embodiments relates to a method for characterizing a library of a plurality of cell strains having different variable regions in at least one part of the genetic material of the cell strains. The method comprises culturing cells of the cell strains at spatially defined and separated positions in a culturing device. A phenotypic characteristic is determined of each cell strain in the culturing device. The cells of the cell strains are fixated at the spatially defined and separated positions in the culturing device. The method also comprises in situ genotyping the variable region of each cell strain at the spatially defined and separated positions in the culturing device. Each respective phenotypic characteristic is then connected to each respective genotype based on the spatially defined and separated positions in the culturing device.

Another aspect of the embodiments relates to a system for characterizing a library of a plurality of cell strains having different variable regions in at least one part of the genetic material of the cell strains. The system comprises a culturing device configured to culture cells of the cell strains at spatially defined and separated positions in the culturing device. The system also comprises a first kit comprising components for in situ genotyping the variable region of each cell strain following fixation of the cells at the spatially defined and separated positions in the culturing device. A respective phenotypic characteristic of each cell strain can then be connected to each respective genotype based on the spatially defined and separated positions in the culturing device.

The present embodiments enable parallel phenotypic and genotypic characterization of large libraries of cells. The embodiments further allow various phenotypes to be monitored and determined for the cells in the culturing device.

The system and culturing device of the embodiments facilitate long single cells phenotyping experiments under constant or variable conditions followed by fixation and application of multiple reagents needed for in situ sequencing without losing cells.

BRIEF DESCRIPTION OF THE DRAWINGS

The embodiments, together with further objects and advantages thereof, may best be understood by making reference to the following description taken together with the accompanying drawings, in which:

FIG. 8 illustrates part of the genome of a cell strain according to an embodiment;

FIG. 9 illustrates a mRNA sequence obtained from the part of the genome shown in FIG. 8; and FIG. 10 illustrates a cDNA sequence obtained from the mRNA sequence shown in FIG. 9;

FIG. 11 illustrates part of the genome of a cell strain according to another embodiment; and FIG. 12 illustrates a cDNA sequence obtained from the part of the genome shown in FIG. 11.

DETAILED DESCRIPTION

Figure 1:
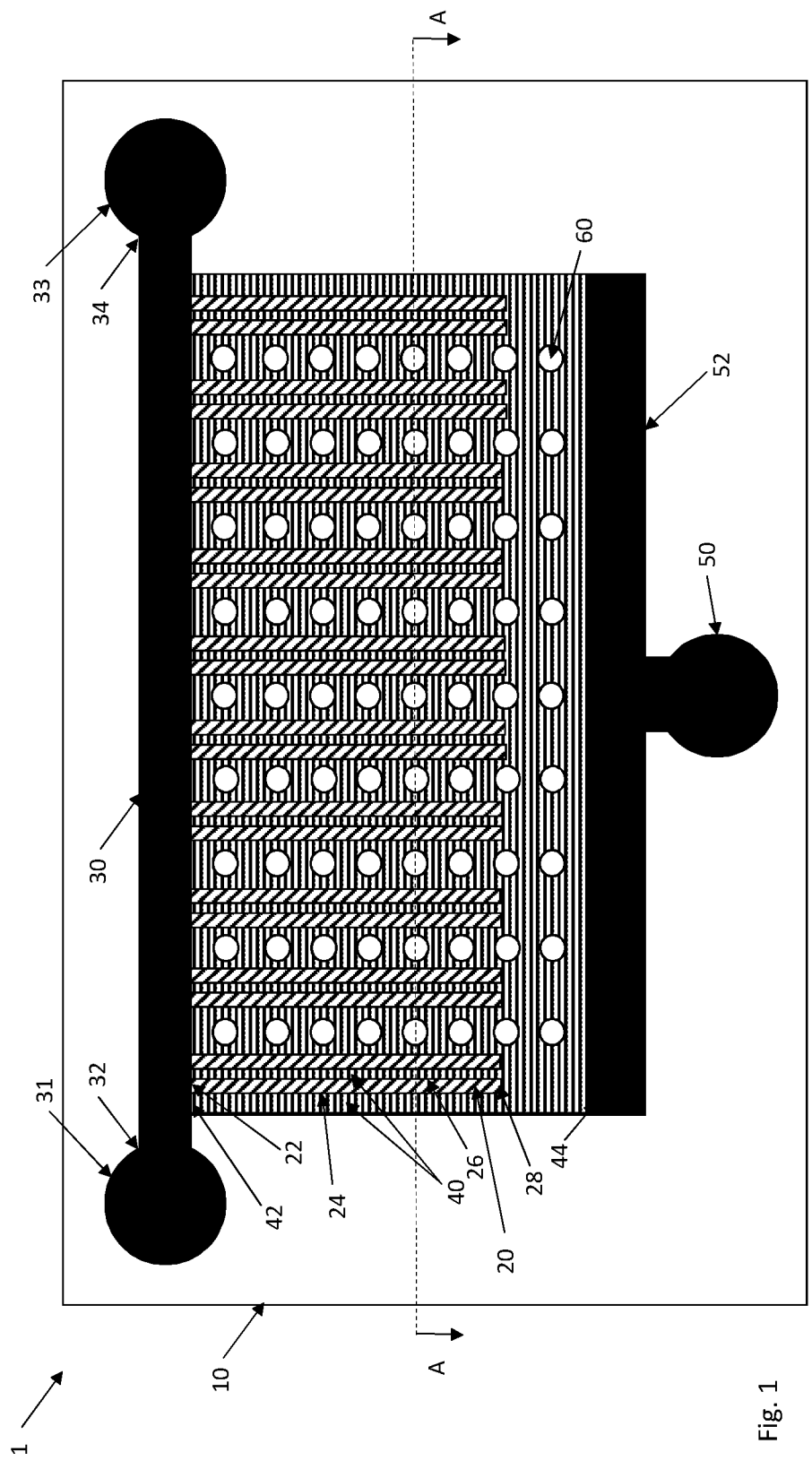
FIG. 1 is an illustration of a culturing device according to an embodiment.

Throughout the drawings, the same reference numbers are used for similar or corresponding elements.

The present embodiments generally relate to phenotypic characterization and in situ genotyping of a library of cell strains. In particular, the present embodiments allow monitored phenotypic characteristics and in situ determined genotypes to be connected in a highly parallel way. This means that a vast library of cell strains with different genotypes can be processed in parallel in order to connect the monitored phenotypic characteristics to the different genotypes of the cell strains.

Cell strain as used herein denotes cells derived from a primary culture or a cell line by selection and cloning of cells having specific genotype. Thus, cells of a cell strain all have the same genotype. A library of cell strains is thereby a collection of genetically different cells. The cell strains in the library of the embodiments can be any cell type including bacterial strains, yeast strains, eukaryotic cell strains, cell lines, primary cells, stem cells, cells in tissues or microcolonies, isogenic cells that are different with respect to mobile deoxyribonucleic acid (DNA) elements, vectors or plasmids that they carry. Cell strains as used herein also encompass multicellular complexes, tissues, etc. as long as these can be cultured in vitro as disclosed herein.

An aspect of the embodiments relates to a method for characterizing a library of a plurality of cell strains having different variable regions in at least one part of the genetic material of the cell strains. The method comprises culturing cells of the cell strains at spatially defined and separated positions in a culturing device. A phenotypic characteristic of each cell strain is determined in the culturing device. The cells of the cell strains are fixated at the spatially defined and separated positions in the culturing device. The method also comprises in situ genotyping the variable region of each cell strain at the spatially defined and separated positions in the culturing device. Each respective phenotypic characteristic is then connected to each respective genotype based on the spatially defined and separated positions in the culturing device.

The library of cell strains can be obtained according to various techniques within genome engineering. For instance, Multiplex Automated Genomic Engineering (MAGE) can be used to create several billions of different mutant genomes per day (Wang et al. *Nature*, 2009, 460: 894-898). Other techniques that can be used to create a library of cells include Clustered Regularly Interspaced Short Palindromic Repeats (CRISPR) associated protein 9 (Cas9) (Wang et al., *Science*, 2014, 343: 80-84; Koike-Yusa et al., *Nature Biotechnology*, 2014, 32: 309-312; Zhou et al., *Nature*, 2014, 509: 487-491) or large-scale RNA interference (Berns et al., *Nature*, 2004, 428: 431-437).

The present embodiments use a culturing device in which cells of each cell strain in the library can be kept and cultured separately from cells of other cell strains and or other genotypes. Hence, each cell strain has a respectively spatially defined and separated position in the culturing device in which the cells can grow and be studied.

Culture medium or media may advantageously be added to the cells at the spatially defined and separated positions in the culturing device. The culture medium could be continuously added to the cells or is replenished or exchanged periodically or at selected time instances. The media exchange is preferably in such a way that excess cells do not attach and contaminate the spatially defined and separated positions of cells of other genotypes.

The cells are preferably allowed to be cultured and grown in a monolayer at the spatially defined and separated positions in the culturing device. A monolayer is generally preferred over 3D structures or matrices in terms of that is typically easier to monitor the cells and determine phenotypic characteristics of the cells if they are present in a monolayer. However, cells can be grown in structures that support 3D growth if phenotypes related to, for instance, cell-to-cell interactions are monitored, such as for instance in differentiation or development.

The cells cultured at the spatially defined and separated positions in the culturing device can preferably be exposed to various physical and/or chemical stimuli or agents without being washed away, in order to monitor the response of the cells to the physical and/or chemical stimuli or agents. For instance, various chemical test agents, such as nutrients, drugs, antibiotics, gene expression inducers or repressors, could be added to the culture medium and thereby contact the cells. The phenotypic characteristics of the cell strains in terms of the response of the cells of the different cell strains to the various test agents can then be determined, for instance, using microscopy. Correspondingly, the temperature, pH, pressure, flow, gases, light exposure or mechanical stress that the cells are exposed to could be changed and the response of the cells of the different cell strains to such changing physical conditions can be determined, for instance, using microscopy.

The cells strains have different genotypes as represented by having different variable regions in at least one part of their genetic material. The variable region is typically present in the genome of the cell strains. Alternatively, the variable region is present in a mobile genetic element, such as plasmid or vector, and hence does not necessarily have to be stably incorporated into the genome of the cells. In the following, the embodiments are mainly discussed with regard to the variable region being present in the genome. However, alternative embodiments are possible where the variable region and the further DNA elements mentioned herein are instead present in a plasmid or other mobile genetic element of the cell strains. The variable region, or parts thereof, can also be present in unstable genetic elements, such as transposons, viruses or phages. Such encoding will sometimes have advantages in terms of amplifying the variable sequence before fixing the cells for in situ sequencing, for example by specifically excising or circularizing parts of the variable region from the dsDNA genome before fixing the cells.

Various culturing devices that can be used according to the embodiments will be further described herein.

In an embodiment, the method also comprises randomly seeding cells of the cell strains at the spatially defined and separated positions in the culturing device. The randomly seeding of cells is preferably performed so that each spatially defined and separated position only comprises cells of a same genotype, i.e. of the same cell strain.

An advantage of the embodiments is that the genetic identity, i.e. genotype, of the cells does not need to be determined and known prior to seeding of the cells in the culturing device. Thus, there is no need to keep the cells in the cell library sorted prior to seeding in terms of having to know the genetic identity of each cell strain and continuously monitoring the position of each genotype throughout the method. This means that the present embodiment in clear contrast first analyzes the phenotypic characteristics in parallel without any knowledge of the genotype and then determines the genotypes and connects them to the phenotypic characteristics.

By in situ sequencing individual cell strains it is possible to grow the different strains much denser than what would be possible if, for example, specific barcoded sequencing primers would be distributed to the spatially separated positions before or after phenotyping.

The random seeding can thereby be performed by letting individual cells from a library generated in bulk settle at spatially defined and separated positions and form a microcolony of isogenic cells.

In an alternative approach, the random seeding can be performed by adding cells of a first cell strain in the library to a first spatially defined and separated position in the culturing device, a second cell strain in the library to a second spatially defined and separated position in the culturing device, and so on until all cell strains to be monitored have been distributed among the different spatially defined and separated positions in the culturing device.

The phenotypic characteristic determined for each cell strain in the library is preferably a phenotypic characteristic corresponding to each genotype in the library. Thus, the cells in the library are genetically different cells having different genotype, i.e. a respective genotype per cell strain. The differences in genotype imply that the cells will have different phenotypic characteristics corresponding to each respective genotype.

In an embodiment, the phenotypic characteristics of the cells are determined using microscopy. Microscopy for monitoring and determining phenotypes has several advantages as compared to prior art technologies. For instance, fluorescence microscopy allows for extensive time laps of cell linages over many generations, single molecule detection sensitivity and the possibility to monitor temporal responses to changing growth conditions in any way. Thus, it is possible to monitor the phenotype of the cell lines in parallel over an extended period of time and not only at a single time point as in FACS.

Non-limiting but illustrative examples of phenotypic characteristics that can be monitored and determined according to the embodiments using microscopy include cell morphology, spatial and/or temporal expression patterns of various molecules, such as ribonucleic acid (RNA) or proteins, levels of specific metabolites, lifespan or growth rate changes, such as in response to addition of different physical or chemical stimuli or agents, cell-to-cell variations in gene expression levels, embryo development, brightness of reporter proteins or RNA aptamers, etc.

The phenotypic characterization of the cell strains can, thus, be performed in parallel under a microscope for a long period of time if needed. The phenotypic characterization is furthermore performed without knowledge of the genotype of the various cell strains in the library. In clear contrast, the phenotypic characterization instead determines respective phenotypic characteristics for each spatially defined and separated position in the culturing device. For instance, assume that the relevant phenotypic characteristic to be determined for the cell strains is gene expression of a target gene for a fluorescence reporter protein, with a variable gene regulatory region or coding sequence, following addition of a test agent. In such a case, the microscope can be used to take an image over the culturing device in which the respective gene expression levels can be visually determined. Each individual gene expression level can then be quantized to get a respective value for each spatially defined and separated position in the culturing device. Thus, the output of the determination of the phenotypic characterization could be a list or matrix of one or more respective values for each spatially defined and separated position in the culturing device.

It is advantageously if the spatially defined positions are labeled, numbered or marked so that it is easy to define the relationship between spatially defined position and phenotype, i.e. which spatially defined position corresponds to which phenotype. It could also be possible to define the spatial position in relation to the distance or order among the spatially defined positions.

For instance, a list could be in the form of position 0=value 0, position 1=value 1, position 2=value 2, and so on. A matrix may correspondingly be in the form of position (x, y)=value 0, position (x+1, y)=value 1, and so on.

In an embodiment, determining the phenotypic characteristic comprises determining the phenotypic characteristic of each cell strain during culturing of the cells in the culturing device using microscopy. Examples of microscopy technologies that can be used in the embodiments include, for instance, bright field microscopy, phase contrast microscopy, fluorescence microscopy, light sheet microscopy, or any type of super resolution imaging modality such as stimulated emission depletion (STED) microscopy, photoactivated localization microscopy (PALM), near-field scanning optical microscopy (NSOM), 4Pi microscopy, structured illumination microscopy (SIM), ground state depletion (GSD) microscopy, spectral precision distance microscopy (SPDM), stochastic optical reconstruction microscopy (STORM). Furthermore, Intracellular Single Particle Tracking (SPT) or Fluorescence Correlation Spectroscopy (FCS) could also be used. Microscopy analysis can be made at fixed time points or using time lapse imaging.

Other measurements of the phenotypes are also possible, such as measuring mechanical properties using atomic force microscopy, membrane potential using indicator dyes or micro electrodes, small molecule secretion using imaging mass spectrometry or specified biosensor arrays. Near-field optical array detectors directly connected to the culturing device are also possible.

Once the phenotypic characteristics of the cell strains have been determined the cells are preferably fixated at the spatially defined and separated positions in the culturing device. Cell fixation can be performed according to techniques well known in the art. For instance, formaldehyde can be used for cell fixation. In a non-limiting example cells are fixed with 4% formaldehyde for about 15 minutes or 3% (w/v) paraformaldehyde in phosphate buffered saline (PBS) for about 30 minutes.

In an embodiment, the fixated cells are permeabilized prior to in situ genotyping. Various protocols traditionally employed for cell permeabilization can be used according to the embodiments. For instance, Triton X-100 (such as 0.25% Triton X-100) or another surfactant, such as nonionic surfactant, can be used. Alternatively, ethanol, such as 70% ethanol, can be used for cell permeabilization. Further examples include hydrochloric acid, such as 0.1 M hydrochloric acid, optionally combined with a protease, such as pepsin, e.g. 0.01% pepsin, or lysozyme to degrade the bacterial cell wall.

In an embodiment, the cells are induced to express or activate one or more enzymes to modify or amplify the variable sequence or parts thereof before fixation. Non limiting examples include activation or deactivation of transcription factors or RNA polymerases that lead to transcription of a barcode and neighboring sequences into RNA, restriction enzymes that cut the variable sequence from chromosomal DNA, transposases that excide DNA including the variable sequence, ligases that ligates ssDNA or dsDNA to form templates for rolling circle amplification, etc.

The in situ genotyping comprises in situ genotyping at least a part of the variable region of each cell strain at the spatially defined and separated positions in the culturing device. Hence, it is not absolutely necessary to in situ genotype the complete variable region of each cell strain. Hence, in situ sequencing as used herein comprises in situ sequencing at least a part of the variable region or indeed the complete variable region. The in situ sequencing preferably outputs information showing any nucleotide differences in the variable region between different cell strains and where these nucleotide differences give rise to different phenotypes.

In an embodiment, in situ genotyping is based on the technology fluorescent in situ sequencing (FISSEQ) as described for example in *Science,* 2014, 343(6177): 1360-1363. Briefly, in FISSEQ cDNA amplicons within the cell are generated in the fixed cells using reverse transcriptase and incorporation of aminoallyl deoxyuridine 5'-triphosphate (dUTP) during reverse transcription (RT). The cDNA is refixed using BS(PEG) 9, an amine-reactive linker with a 4 nm spacer. The cDNA fragments are then circularized before rolling circle amplification (RCA). BA(PEG)9 is then used to cross-link the RCA amplicons containing aminoallyl dUTP. SOLiD sequencing by ligation can then be used to sequence the relevant sequence in the RCA amplicons to get the nucleotide sequence of the variable region.

In an embodiment, in situ genotyping the variable region preferably comprises in situ sequencing by ligation of the variable region or at least a portion thereof at the spatially defined and separated positions in the culturing device. Sequencing by ligation relies upon the sensitivity of deoxyribonucleic acid (DNA) ligase for base pair mismatches. Generally, the variable region to be sequenced is preferably in the form of a single stranded DNA sequence, flanked on at least one end by a known sequence that will function as anchor primer-binding sequence. An anchor primer that is complementary to the known sequence is brought to bind to the known sequence.

A mixed pool of probe oligonucleotides, typically eight to nine bases long, is then brought in, labelled, typically with a fluorescent dye, according to the position that will be sequenced. These labelled oligonucleotides hybridize to the variable region, next to the anchor primer and DNA ligase preferentially joins an oligonucleotide to the anchor primer when its nucleotide sequence matches the unknown variable region. Based on the fluorescence produced by the molecule, one can infer the identity of the base at this position of the variable region.

The oligonucleotide probes may also be constructed with cleavable linkages, which can be cleaved after identifying the label. This will both remove the label and regenerate a 5'-phosphate on the end of the ligated probe, thereby enabling a new round of ligation. This cycle of ligation and cleavage can be repeated several times to read longer sequences. This technique sequences every $N^{th}$ base in the variable region, where N is the length of the probe left behind after cleavage. In order to sequence the skipped positions in the variable region, the anchor primer and the ligated oligonucleotides may be stripped of the variable region, and another round of sequencing by ligation is started with an anchor primer that is one or more bases shorter.

Another technique is to do repeated rounds of a single ligation where the label corresponds to different positions in the probe, followed by stripping the anchor primer and ligated probe.

Sequencing by ligation can be proceeded in either direction (5'-3' or 3'-5') depending on which end of the oligonucleotide probes that is blocked by the label.

In an embodiment, the sequence that is sequenced is preferably a complementary DNA (cDNA) sequence obtained by reverse transcription of an RNA transcript obtained from the variable region. In this embodiment, the variable region is flanked by at least one known sequence to which the anchor primer will bind.

Sequencing by ligation can be performed on fixated cells to achieve an in situ sequencing by ligation of the variable region or at least a portion thereof at the spatially defined and separated positions in the culturing device, see for instance *Science* 2014, 343: 1360-1363 and *Nature Methods* 2013, 10: 857-860, the teachings of which are hereby incorporated by reference with regard to performing in situ sequencing by ligation.

Briefly, in one variant, RNA obtained from the variable region, or a barcode see further below, is copied to cDNA by reverse transcription, followed by degradation of the mRNA strand using an RNase.

In a first embodiment, a padlock probe binds to the cDNA with a gap between the probe ends over the bases that are targeted for sequencing by ligation. This gap is filled by DNA polymerization and DNA ligation to create a DNA circle.

In a second embodiment, cDNA circulation is carried out by ssDNA ligation only.

In a third embodiment, dsDNA including at least a part of the variable sequence and neighboring DNA is excised from the surrounding DNA, by for example restriction enzymes or transposases. The excised dsDNA can then be digested to ssDNA by endonucleases in order to self-hybridize and ligate to form a circular DNA.

In either case, the formed DNA circle is amplified by target-primed rolling circle amplification (RCA) generating a rolling circle product (RCP) that is subjected to sequencing by ligation. An anchor primer is hybridized next to the targeted sequence before the ligation of oligonucleotides probes. In an embodiment, the oligonucleotide probes consist of four libraries of 9-mers, with eight random positions (N) and one fixed position (A, C, G or T). Each library is labeled with one of four fluorescent dyes. The oligonucleotide probe with best match at the fixed position will be incorporated by ligation along with its fluorescent label. The sample is imaged and each RCP displays the color corresponding to the matched base. The oligonucleotide probe is washed away before the application of oligonucleotide probes for the next base. The steps of ligation, washing, imaging and stripping are iterated until the desired number of bases has been read.

In another embodiment, in situ genotyping comprises in situ sequencing by synthesis of the variable region or at least a portion thereof at the spatially defined and separated positions in the culturing device.

For instance, four types of modified dNTPs containing a terminator that blocks further polymerization are added. The terminator also contains a fluorescent label that can be detected by camera. Non-incorporated nucleotides are washed away and images of the fluorescently labeled nucleotides are taken. The fluorescent label along with the terminator are chemically removed from the DNA allowing for the next cycle of sequencing to being.

The result of the in situ genotyping is preferably the nucleotide sequence of the variable region or at least a portion thereof for each cell strain. Each nucleotide sequence is furthermore connected to a respective spatially defined and separated position in the culturing device. This is possible since the genotyping is performed as an in situ genotyping, such as in situ sequencing by ligation or synthesis. In situ here implies that the genotyping is performed on site or in position, i.e. in the spatially defined and separated positions in the culturing device.

The output of the previously described phenotyping was a respective determined phenotypic characteristic for each spatially defined and separated position in the culturing device, such as in the form of a list or matrix listing the phenotypic characteristic(s) determined for each spatially defined and separated position.

The output of the in situ genotyping is the nucleotide sequence determined for the variable regions at each spatially defined and separated position in the culturing device. This output may also be in the form of a list or matrix listing the nucleotide sequence determined for each spatially defined and separated position.

For instance, a list could be in the form of position 0=sequence 0, position 1=sequence 1, position 2=sequence 2, and so on. A matrix may be in the form of position (x, y)=sequence 0, position (x+1, y)=sequence 1, and so on.

Each respective phenotypic characteristic can then be connected or associated with each respective genotype based on the spatially defined and separated positions in the culturing device. For instance, the phenotypic characteristic determined for the cells of the cell strain at position 0 in the culturing device is a result of the genotype of the cells of this cell strain and this genotype is obtained from the nucleotide sequence determined for position 0. Hence, the connection of phenotype and genotype can be achieved simply by matching the phenotypic characteristics and genotypes determined for each spatially defined and separated position in the culturing device.

In an embodiment, each cell strain has a respective strain-specific barcode sequence 140 in its genetic material, preferably in its genome 100, see FIG. 8. In such a case, the in situ genotyping preferably comprises determining the respective genotype by in situ sequencing at least a part of the respective barcode sequence 140 of each cell strain at the spatially defined and separated positions in the culturing device 1.

Thus, the barcode sequence 140 provides a bridge to the determination of the variable region 150 in a cell strain. In particular, the in situ genotyping can be performed by in situ sequencing, such as in situ sequencing by ligation or synthesis, the comparatively much shorter barcode sequence 140 instead of sequencing the variable region 150. The nucleotide sequence of the variable region 150 can then be obtained based on the sequenced barcode sequence 140 and mapping information as described below.

The method preferably comprises determining mapping information specifying a connection between each variable region 150 and a respective barcode sequence 140. Determining the respective genotype then preferably comprises determining the respective genotype based on the in situ sequenced at least a part of the respective barcode sequence and the mapping information.

The mapping information can thereby be regarded as a look-up table that outputs the nucleotide sequence of a variable region 150 given an input nucleotide sequence of at least a part of a barcode sequence 140. The mapping information could thereby be in the form of a table listing the respective barcode sequence 140 for each variable region 150.

The mapping information can be obtained in connection with producing the library of cell strains. For instance, genome engineering can be used to generate large libraries of cell strains with genetic diversity with regard to the variable region 150 as represented by various point mutations 155 in FIG. 8. Such technology can also be used to tailor respective barcode sequences 140 for the different variable regions 150. For instance, the library of cell strains could be designed so that barcode sequence no. 1 is included in the genome 100 of the cell strain having variable sequence no. 1, and so forth. This typically requires that the barcode 140 is embedded in the variable region 150 or in its immediate proximity.

In another embodiment, the barcode sequence 140 and the variable region 150 are not introduced at the same reaction. The mapping information may then be determined by sequencing the library of cell strains in bulk to obtain, for each cell strain, a sequence read encompassing the variable region 150 and the respective specific barcode sequence 140. This allows the barcode sequence 140 to be as far away from the variable region 150 as is it is possible to make in a single sequencing read.

Thus, the relevant region of the genome or chromosome of most cells in the library is sequenced in bulk in such a way that individual reads encompass the variable region 150 and the barcode sequence 140. The result of the bulk sequencing is thereby the nucleotide sequence of the sequence read for each cell strain. This information can thereby be stored and used as mapping information.

The barcode sequence 140 can also be introduced in another position in a chromosome or be maintained in a mobile genetic element, such as a plasmid. In these cases the barcode sequence 140 is connected to the variable region 150 by the method of introducing the variable region 150 and barcode sequence 140 into the cell at the same time. For example, the variable region 150 can be delivered to the cells as a part of a plasmid that also carries the corresponding barcode sequence 140.

In an embodiment, each cell strain has a construct comprising a respective strain-specific barcode sequence 140 and the variable region 150 in its genome 100 flanked by library-common primer-binding sequences 160, 170 of know nucleotide sequence. The library-common primer-binding sequences 160, 170 can be used to amplify the respective strain-specific barcode sequence 140. Alternatively, the at least one library-common primer-binding sequence 160, 170 can be used to sequence the respective strain-specific barcode sequence 140 directly from the genome 100 or via a transcribed RNA sequence 200, see FIG. 9, that is reverse transcribed into a cDNA sequence 300, see FIG. 10.

Hence, in this embodiment each cell strain has a barcode sequence 140 in its genome 100 or a mobile genetic element. This barcode sequence 140 is advantageously created together with the variable region 150 when creating the library of cell strains as previously described herein. The barcode sequence 140 is strain-specific implying that each cell strain, i.e. genotype or version of the variable region 150, has its own specific nucleotide sequence for the barcode sequence 140. Thus, the library preferably does not contain two different cell strains with different variable regions 150 but having the same barcode sequence 140.

In contrast to the strain-specific barcode sequence 140, the at least one primer-binding sequence 160, 170 is preferably library-common or strain-common implying that this at least one primer-binding sequence 160, 170 preferably has the same nucleotide sequence in all cell strains of the library. Hence, one and the same primer or primer pair that is complementary to the primer-binding sequence 160 or sequences 160, 170 can thereby be used for amplification or sequencing purposes in all cell strains.

In a first embodiment, the construct comprises one library-common primer-binding sequence 160, 170. In such a case, the library-common primer-binding sequence 160 could be provided upstream of the barcode sequence 140 (and the variable region 150) or the library-common primer-binding sequence 170 is downstream of the barcode sequence 140 (and the variable region 150).

In a second embodiment, the construct comprises two library-common primer-binding sequences 160, 170. In such a case, one is preferably provided upstream of the barcode sequence 140 (and the variable region 150) and the other is positioned downstream of the barcode sequence 140 (and the variable region 150) as shown in FIG. 8. These two library-common primer-binding sequences 160, 170 can then be used as binding sites for a padlock probe around the barcode sequence 140.

FIG. 8 illustrates an example of a portion of the genome 100 in a cell strain of the library. FIG. 9 represents a transcribed RNA sequence 200 or mRNA sequence 200 obtained by transcribing the construct with the strain-specific barcode sequence 140, the variable region 150 and the at least one library-common primer-binding sequence 160, 170. FIG. 10 represents a cDNA sequence 300 obtained by reverse transcribing the RNA sequence 200 of FIG. 9.

In FIGS. 8-10 reference numbers 1X0, 2X0, 3X0 have been used, with X=3-7 to represent the corresponding nucleotide sequence portions in the genome 100, in the transcribed RNA sequence 200 or in the cDNA sequence 300.

FIG. 8 additionally shows a promoter sequence 110 used to transcribe the construct comprising the strain-specific barcode sequence 140, the variable region 150 and the at least one library-common primer-binding sequence 160, 170. The genome 100 may optionally comprise at least one regulatory sequence 120, which controls the promoter sequence 110 and transcription of the construct.

In an embodiment, the library-common primer-binding sequences 160, 170 are used to amplify the strain-specific barcode sequence 140 and optionally also the variable region 150, for instance by in situ polymerase chain reaction (PCR). The amplification of at least the strain-specific barcode sequence 140 may be advantageous prior to in situ sequencing the strain-specific barcode sequence 140 in order to get a sufficient copy number of the strain-specific barcode sequence 140 to perform the in situ sequencing.

The amplification can be performed directly on the genome sequence 100 in the cell libraries. However, it may be preferred to first perform in situ reverse transcription of the transcribed RNA sequence 200 obtained by transcribing the construct with the strain-specific barcode sequence 140, possibly the variable region 150 and the at least one library-common primer-binding sequence 160, 170 in the genome 100. In such a case, a DNA primer 360 complementary to a library-common primer-binding sequence 260 in the RNA sequence 200 is added together with a reverse transcriptase or an RNA-dependent DNA polymerase to in situ generate the cDNA sequence 300 as schematically illustrated in FIG. 9. The amplification is then made of the generated cDNA sequence 300.

The amplification may, in an embodiment, be in the form of in situ amplification of the cDNA sequences 300 by rolling circle amplification (RCA) following circulation using single-stranded DNA (ssDNA) ligase or hybridization and ligation of a padlock probe. Alternatively, the in situ amplification of the cDNA sequences 300 can be performed by in situ PCR.

Usage of a padlock probe in order to form a circular DNA sequence from a cDNA sequence is described in *Nature Methods* 2013, 10: 857-860, see for instance FIG. 1 in that document.

The resulting cDNA sequence 300 can then be amplified by means of a DNA polymerase and a DNA primer complementary to a library-common primer-binding sequence 360 in the cDNA sequence 300. In situ sequencing of the strain-specific barcode sequence 360 in the resulting cDNA sequences 300 can then take place as further described herein.

In an embodiment, the method comprises in situ amplifying the respective strain-specific barcode sequence 140 or in situ sequencing the respective strain-specific barcode sequence 140 from the genetic material 100 by rolling circle amplification following excision, preferably in situ or in vivo excision, the respective strain-specific barcode sequence 140 from the genetic material 100.

The respective strain-specific barcode sequence 140 is preferably excised from the genetic material 100 using digestion or transpose activity. The method preferably also comprises making ssDNA from the excised strain-specific barcode sequence 140 in an exonuclease reaction and circulation by hybridizing a padlock probe, or by ssDNA ligation or by dsDNA ligation following self-hybridization.

The at least one library-common primer-binding sequence 160, 170 can alternatively, or in addition, be used to sequence the respective strain-specific barcode sequence 140 from the genome 100. In such a case, the library-common primer-binding sequence 160 will correspond to the anchor primer-binding sequence for in situ sequencing by ligation or primer-binding sequence for in situ sequencing by synthesis.

The in situ sequencing may be performed directly on the genome 100 of the cell strains as described above. However, it is generally preferred to generate cDNA sequences 300 by reverse transcribing RNA sequences 200 obtained by transcribing the construct in the genome 100 comprising the strain-specific barcode sequence 140, the variable region 150 and the at least one library-common primer-binding sequence 160, 170. In such a case, it is possible to in situ amplify the cDNA sequences 300 prior to starting the in situ sequencing of the strain-specific barcode sequences 340.

It is also possible to amplify the genomic region including the barcode sequence 140 directly by using an isothermal amplification technique, such as loop-mediated isothermal amplification (LAMP), strand displacement amplification (SDA), helicase-dependent amplification (HAD) or nicking enzyme amplification reaction (NEAR).

In another embodiment, a RCA template is formed by letting the cDNA 300 self-ligate by using reverse transcription primers that mediate hybridization of the two ends and consecutive ligation. For instance, the cDNA 300 is ligated after it has self-hybridized to a nicked double stranded DNA over, preferably, at least 6 basepairs.

In an embodiment the method comprises synthesizing, for each cell strain, a cDNA sequence 300 from a transcribed RNA sequence 200 using primers 360 complementary to at least one library-common primer-binding sequence 260 in the transcribed RNA sequence 200 and a reverse transcriptase or an RNA-dependent DNA polymerase. In such a case, the in situ sequencing preferably comprises in situ sequencing at least a part of the respective strain-specific barcode sequence 340 in the cDNA sequence 300 of each cell strain at the spatially defined and separated positions in the culturing device 1.

The in situ sequencing can be performed by in situ sequencing by ligation or by synthesis of at least a part of the respective strain-specific barcode sequence 340.

The in situ sequencing of the strain-specific barcode sequences 340 can be performed using the previously mentioned at least one library-common primer-binding sequence 360, 370. Alternatively, a dedicated sequencing primer-binding sequence 130 could be provided in the genome 100, preferably directly upstream of the barcode sequence 140. This sequencing primer-binding sequence 130 preferably has known nucleotide sequence and is advantageously library-common for all cell strains in the library.

In this approach, the at least one library-common primer-binding sequence 160, 170 is mainly used for reverse transcription and amplification purposes, whereas the sequencing primer-binding sequence 130 is used for in situ sequencings of the strain-specific barcode sequences 140.

In a specific implementation only the barcode sequence 140 is transcribed along with flanking sequences 160, 170 for amplification or circularization of the corresponding cDNA, see FIG. 11. The transcribed barcode sequence 140 is integrated at a distance from the variable region 150, but the mapping between the variable region 150 and the barcode sequence 140 can be obtain through individual sequencing reads when the corresponding region of the cell library is sequenced in bulk. The advantage of this implementation is that the barcode sequence 140 and its flanking regions 160, 170 can be selected independent of the organization of the variable region 150 as long as the barcode sequence 140 has a much greater diversity than the variable region 150. For example a 15 base pair (bp) random barcode sequence will allow $4^{15}\sim10^9$ different barcode combinations. If the corresponding variable region has $10^6$ variants, the risk is only 0.001 that one barcode sequence match two different variable regions.

FIG. 12 illustrates a cDNA sequence 300 obtained from the transcribed portion of the genome 100 shown in FIG. 11. The two library-common primer-binding sequences 360, 370 flanking the barcode sequence or region 340 in the cDNA sequence 300 can be used for amplification, padlock probing or anchor-primer ligation as previously described herein.

Once the nucleotide sequence of the strain-specific barcode sequence 140 has been determined the mapping information can be used to get the corresponding nucleotide sequence of the variable region 150 that matches this particular strain-specific barcode sequence 140. This is preferably performed for each cell strain in the library to determine the different genotypes. The result is thereby a respective genotype for each spatially defined and separated position in the culturing device. The genotypes are then matched or connected to the previously determined phenotypic characteristics to thereby provide information of the particular genotypes that resulted in the determined phenotypic characteristics in the library of cell strains.

In an embodiment, the library of cell strains is characterized by that the different cell strains expresses different RNA products from differentially barcoded extra chromosomal genetic elements. The RNA products could, for instance, be mRNA, iRNA, or guide RNA for dCas9.

Another aspect of the embodiments relates to a system for characterizing a library of a plurality of cell strains having different variable regions in at least one part of the genome of the cell strains. The system comprises a culturing device configured to culture cells of the cell strains at spatially defined and separated positions in the culturing device. The system also comprises a first kit comprising components for in situ genotyping the variable region of each cell strain following fixation of the cells at the spatially defined and separated positions in the culturing device. With such a system, a respective phenotypic characteristic of each cell strain can be connected to each respective genotype based on the spatially defined and separated positions in the culturing device.

In an embodiment, the system also comprises a microscope configured to determine a phenotypic characteristic and a genotype of each cell strain in the culturing device. Thus, a microscope of the system is used to monitor and determine the respective phenotypic characteristics of the cell strains at the respective spatially defined and separated positions in the culturing device. The microscope is preferably also used during in situ sequencing in order to read out fluorescent signals.

In an embodiment, the system also comprises the library of the plurality of cell strains. This library of cell strains can be generated as previously described herein using techniques for genome engineering to generate a large library of different genotypes.

In such a library the mapping between the variable region and the barcode sequence will be provided, such that preferably only the barcode sequence needs to be sequenced in order to determine the genotype.

The library can for example be based on conditional repression or activation of the activity for each gene in cells from a specific organisms. For example the variable region can encode one or a few short guide RNAs for each transcribed region in the organism, such that the gene activity of individual genes can be altered by a dCas9 mediated regulation.

The culturing device of the system can be constructed according to various embodiments. In an embodiment, the culturing device is a culturing device or plate comprising a plurality of wells, patches or compartments, preferably at least one well, patch or compartment per cell strain of the library. For instance, cell plates having several thousands of wells, such as 96×96 wells, are available on the marked for cell culturing purposes. Such cell plates can be used as culturing device in the embodiments. In such a case, each well corresponds to a spatially defined and separated position in the culturing device. The culture plate is preferably of plastic material or glass that is transparent for imaging or is built directly on a spatially addressable biosensor or light detector array.

In another embodiment, the culturing device is a substrate having a plurality of spatially defined and separated patches where cells of the cell strains can adhere and grow. The substrate is preferably made of a plastic material or glass that is transparent for imaging. The substrate may, in an embodiment, be in the form of a microscope slide having a plurality of micro-wells constituting the spatially defined and separated positions in the culturing device. The surface of the micro-wells may optionally be treated or coated for facilitating cell adherence.

An alternative approach is to have a microscope slide or other substrate having a plurality of patches that constitute respective portions of the microscope slide or other substrate that have been surface treated or coated to facilitate and promote cell adherence. This means that cells of the library will easily adhere to and grow on the patches whereas the cells do not efficiently adhere to intermediate surface portions of the microscope slide or other substrate lacking the adherence-promoting surface treatment or coating. This means that by adding culture media to the microscope slide or other substrate any cells present on the intermediate surface portions will be flushed away, whereas cells growing on the patches remain firmly attached to the surface. When seeded sparsely this format will support the growth of isogenic cells at each patch.

Patches or wells can be coated with for example polylysine, collagen, fibronectin, lamninin and/or gelatin.

More information of culturing devices that can be used according to the embodiments can be found in Wang et al. *Current Biology* 20, 1099-1103, 2010.

In an embodiment, the culturing device is a microfluidic device 1, see FIGS. 1-7. The microfluidic device 1 comprises a substrate 10 transparent for imaging and having a plurality of spatially defined and separated cell channels 20. The cell channels 20 have a dimension to accommodate cells in monolayer. A respective end 22 of the plurality of spatially defined and separated cell channels 20 is in fluid connection with a flow channel 30 having a fluid source 31 in a first end 32 of the flow channel 30 and a fluid sink 33 at a second end 34 of the flow channel 30.

The substrate 10 has multiple cell channels 20 in which cells of the cell strains are cultured. The cell channels 20 may be arranged in parallel as shown in FIGS. 1 and 3-7 with a respective end 22 in fluid connection with the flow channel 30 and extending from this flow channel 30. In order to increase the total number of cell channels 20, the cell channels 20 may extend from either longitudinal side of the flow channel 30 thereby substantially doubling the number of cell channels 20 as compared to only having cell channels 20 on one side of the flow channel 30, see FIG. 6.

Figure 7:
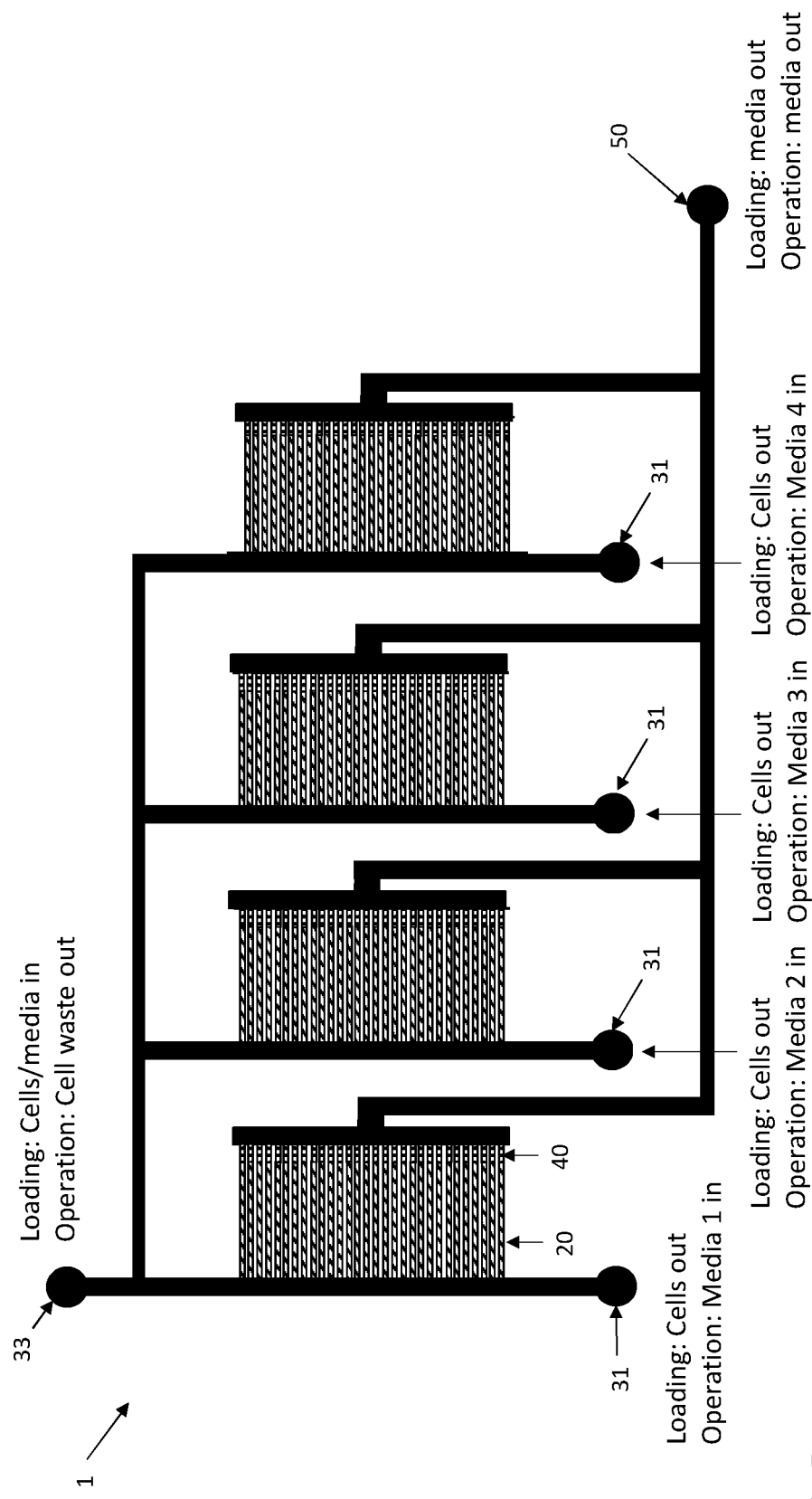
FIG. 7 is an illustration of a culturing device according to a further embodiment.

Also more complex arrangements of cell channels 20 and flow channels 30 are possible in the substrate to increase the number of flow channels 30, see FIG. 7. The important characteristic is that each cell channel 20 has an end 22 in fluid connection with a flow channel 30 and that the cell channels 20 are separated to prevent cells from escaping from one cell channel 20 and entering another cell channel 20.

Figure 2:
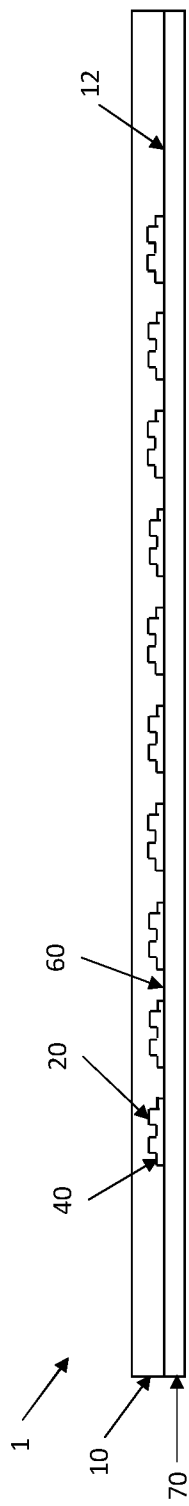
FIG. 2 is a cross-sectional view of the culturing device shown in FIG. 1 along the line A-A.
Figure 4:
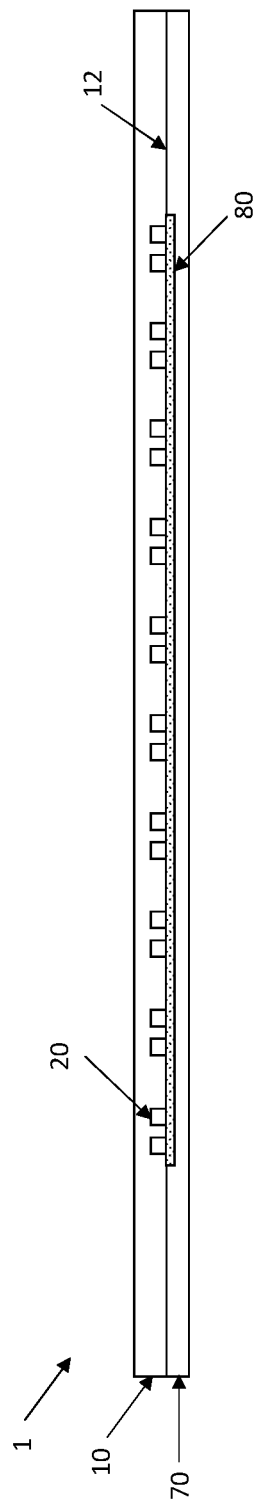
FIG. 4 is a cross-sectional view of the culturing device shown in FIG. 3 along the line A-A.

The cell channels 20 are dimensioned to accommodate cells in monolayer. This means that the height or diameter of the cell channels 20 is selected to be about or slightly larger than the diameter of the cells in the library. For instance, the cell channels 20 could be substantially quadratic in cross-section as shown in FIGS. 2 and 4 with a channel side substantially matching the cell diameter of the cells. Alternatively, the cell channels could have circular or U-shaped cross-section with a diameter substantially matching the cell diameter. Also other cross-sectional configurations are possible as long as the cells could be viably cultured, preferably in monolayer, in the cell channels 20. This implies that the cell channels 20 can be several cells wide but preferentially only one cell high. In this case the cells can grow in the cell channels forming a 2D monolayer that is may be wider than one cell but preferably still is a monolayer. A 2D monolayer generally facilitates phase contrast imaging of the cells as compared to growing the cells in a single line, one cell wide.

The flow channel 30 preferably has dimensions that are significantly larger than the diameter of the cells. This means that any cells entering the flow channel 30 will be flushed through the flow channel 30 towards the fluid sink 33 by a, preferably continuous, flow of culture medium from the fluid source 31 through the flow channel 30 and towards the flow sink 33.

Cells of the library are seeded by adding cells of a respective cell strain in each cell channel 20. The cells are thereby allowed to grow in a monolayer along the length of the cell channels 20. Each cell channel thereby contains cells of a single cell strain and genotype. The cells in the cell channels 20 could be seen as pearls on a string if the cell channel 20 is one cell wide. If the cell channel 20 is wider the cells will form a 2D layer in the cell channel 20.

Cells growing and mitigating past the end 22 of the cell channels 20 will enter the flow channel 30 and are thereby flushed away. The other, opposite end 28 of the cell channels 20 is preferably closed or dimensioned to prevent cells from escaping from this end 28. Alternatively, these ends 28 of the cell channels 20 could be in fluid connection with a second flow channel. In such a case, any cells escaping from the cell channels 20 will be flushed away from the flow of culture medium in this second flow channel.

The fluid source 31 is used to input culture medium into the flow channel 30 and further into the cell channels 20. The culture medium is allowed to exit through the flow sink 33. There is preferably a continuous flow of culture medium from the fluid sink 31 through the flow channel 30 and into the cell channels 20 and out of the fluid sink 33.

The culture medium preferably contains ingredients required by the cells in the library to support viability and optionally also cell growth. The particular culture medium to use depends on the library of cell types and can be selected by the user of the system.

It is also possible to add any chemical agent or drug as test agent to the cells in the cell channels 20 using the fluid source 31, for instance by adding at least one test agent to the culture medium that enters the fluid source 31. In such a case, a phenotypic response of the cell strains to the at least one test agent in the culturing device 1 can be determined, for instance, by microscopy.

The inner surfaces of the cell channels 20 or at least the bottom surface thereof may be surface treated or coated to promote cell adhesion and/or to reduce binding of enzymes and probes in enzymatic steps.

FIG. 1 and FIG. 2, showing a cross-sectional view of the microfluidic device 1 in FIG. 1 along the line A-A, illustrate an embodiment that in relation to state-of-the-art significantly improves flow of culture medium through the cell channels 20 but also promotes cell loading, washing and incubation steps of the cells in the cell channels 20 prior, during and following fixation of the cells in the cell channels 20.

In the illustrated embodiment, each cell channel 20 is flanked along at least one of its longitudinal sides 24, 26 with a respective wash channel 40 having a first end 42 in fluid connection with the flow channel 30 and a second, opposite end 44 in fluid connection with a wash sink 50. The wash channels 40 have a dimension that is too small to accommodate cells.

In an embodiment, each cell channel 20 has at least one wash channel 40 in fluid connection with the cell channel 20 and arranged along one of its longitudinal sides 24, 26. The embodiment as shown FIGS. 1 and 2 have wash channels 40 arranged along both longitudinal sides 24, 26 of each cell channel 20.

In an embodiment, the wash channels 40 may be interconnected, such as at one or both of their ends 44 thereby forming a continuous wash layer around the cell channels 20.

The dimension of the wash channel 40 (or wash layer), such as depth, height and/or width, is too small to accommodate cells. This means that cells present in the cell channels 20 cannot enter the adjacent wash channels 40 but will remain in the cell channels 20. FIG. 2 clearly illustrates the comparatively smaller depth of the wash channels 40 as compared to the cell channels 20. The wash channels 40 may have any cross-sectional configuration, such as quadratic, rectangular, circular, U-shaped, etc.

In an embodiment, the wash channels 40 form a wash layer as shown in FIG. 1. This means that wash channels 40 are present not only along the longitudinal sides 24, 26 of the cell channels 20 but also extend from the respective second ends 28 of the cell channels 20 to the sink channel 52. Thus, a first set of wash channels 40 run along the cell channels 20 and extend from the flow channel 30 to the sink channel 52. A second set of wash channels 40 starts from the second ends 28 of the cell channels 20 and ends at the sink channel 52. The first and second sets of wash channels 40 together form a wash layer.

The cell channel 20 preferably has a substantially same depth when traveling from its first end 22 at the flow channel 30 to its second end 28. This depth preferably corresponds to or is slightly larger than the cell diameter to allow cells in a monolayer in the cell channel 20. At the second end 28 of the cell channel 40 the depth will be shallower when entering the wash channel 40 extending from the second 28 to the sink channel 52. This shallower depth, which preferably is smaller than the cell diameter, prevents cells present in the cell channel 20 from entering the wash channel 40.

Herein follows a short description of the operation of the microfluidic device 1.

During cell loading, the cells with media enter the fluid source 31 and flow into the flow channel 30. In a preferred embodiment, both the fluid sink 33 and the wash sink 40 are open to allow media and cells to be pushed into the cell channels 20. Excess cells are washed out through the fluid sink 33 as the depth of the wash channels 40 (wash layer) is too shallow to allow the cells entering the sink channel 52 and reach the wash sink 50. Media exits the microfluidic device 1 both from the wash sink 50 and the fluid sink 33.

During operation of the microfluidic device 1 culture medium enters the fluid source 31 as described above. In a first embodiment, the wash sink 50 and the fluid sink 33 are open. This means that culture medium will not only exit through the fluid sink 33 but also through the wash sink 50. This means that the culture medium and reagents for in situ sequencing will effectively reach all cells within the cell channels 20. Excess cell will flow into the flow channel 30 and further out from the fluid sink 33, whereas media flow over all the cells and into the sink channel 50 and out from the wash sink 50 to keep all cells supplied with fresh culture medium.

In a second embodiment, the wash sink 50 is closed so that culture medium and excess cells both exit through the fluid sink 33. This is embodiment generally achieves a less efficient flow of cell medium over the cells in the cell channels as compared to the first embodiments.

In wash and reaction steps, the wash sink 50 is preferably open. This means that the wash fluid or liquid or the solution with reaction reagents enters the fluid source 31 and flows through the flow channel 30, the cell channels 20 and the wash channels 40 towards the wash sink 50. In an embodiment, the fluid sink 33 is closed during washing steps. In another embodiment, the fluid sink 33 is open during washing steps. In such a case, wash fluid or liquid may exit through the wash sink 50 or the fluid sink 33.

Washing of cells may take place prior to fixation of the cells in the cell channels 20 to wash away any culture medium, during the fixation of the cells and/or following fixation of the cells to wash away the fixation chemicals, such as formaldehyde. Washing and reaction steps may also be performed in connection with the in situ genotyping when there is a need to change reaction components and reaction medium.

The wash channels 40 are preferably interconnected in their ends 44 by a sink channel 52 that is in fluid connection with the wash sink 50. In the figures, this sink channel 52 goes parallel with the flow channel with the wash channels 40 extending there between. However, whereas the cell channels 20 have one end 22 in fluid connection with the flow channel 30 the other end preferably ends a distance from the sink channel 52 to prevent cells from exiting the cell channels 20 into the sink channel 52. If the wash sink 50 is open during culturing of the cells so that there is a flow of culture medium from the fluid source 31 towards not only the fluid sink 33 but also towards the wash sink 50 this enables uniform growth conditions throughout the cell channel 20.

The cell channels 20 and the wash channels 40 are preferably open channels as shown in FIG. 2. This means that a cover plate 70 is preferably positioned on the substrate 10 to form a lid for and seal the cell channels 20 and the wash channels 40.

The substrate 10 preferably comprises structures or portions 60 extending through the whole thickness of the substrate 10 in order to increase its stability. FIGS. 1 and 2 illustrate such structures 60 in the form of pillars provided in between some of the wash channels 40 along the longitudinal lengths of the cell channels 20. These pillars can have any shape as long as they support the wash layer and provide flow. They could, for example, be rectangular, star shaped, round or triangular and positioned regularly or irregularly. These structures 60 could be separate structures as shown in the figures to promote flow of wash liquid throughout the whole wash layer, i.e. in between wash channels 40. In an alternative approach, each column of pillars shown in the figures forms a single structure extending over the whole length between the flow channel 30 and the sink channel 52. Such a solution may result in a more stable substrate 10, however, at the cost of less efficient washing.

Figure 5:
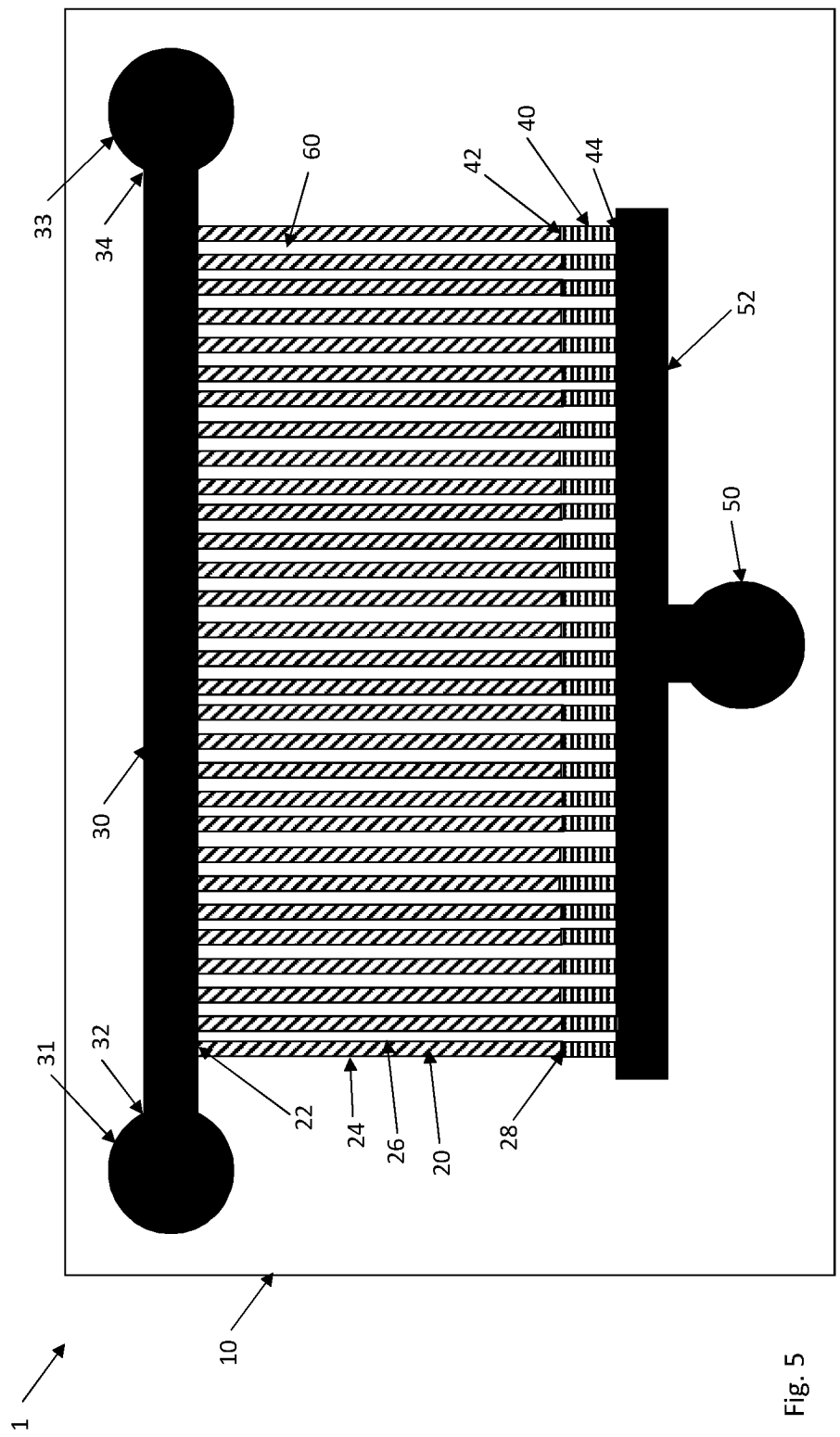
FIG. 5 is an illustration of a culturing device according to a further embodiment.

FIG. 5 illustrates another embodiment of the microfluidic culture device 1. This embodiment lacks the wash channels running along the longitudinal sides 24, 26 of the cell channels 20. In clear contrast, supporting structures 60 are present between adjacent cell channels 20 and extend from the flow channel 30 to the sink channel 52 as shown in the figure. Wash channels 40 are preferably present and extend from the second ends 28 of the cell channels 20 to the sink channel 52. Hence, a wash channel 40 has a first end 42 in fluid connection with a second end 28 of a cell channel 20 and a second, opposite end 44 in fluid connection with the sink channel 52. This embodiment generally provides a more stable microfluidic device 1 as compared to using pillar-like structures as shown in FIG. 1.

Figure 6:
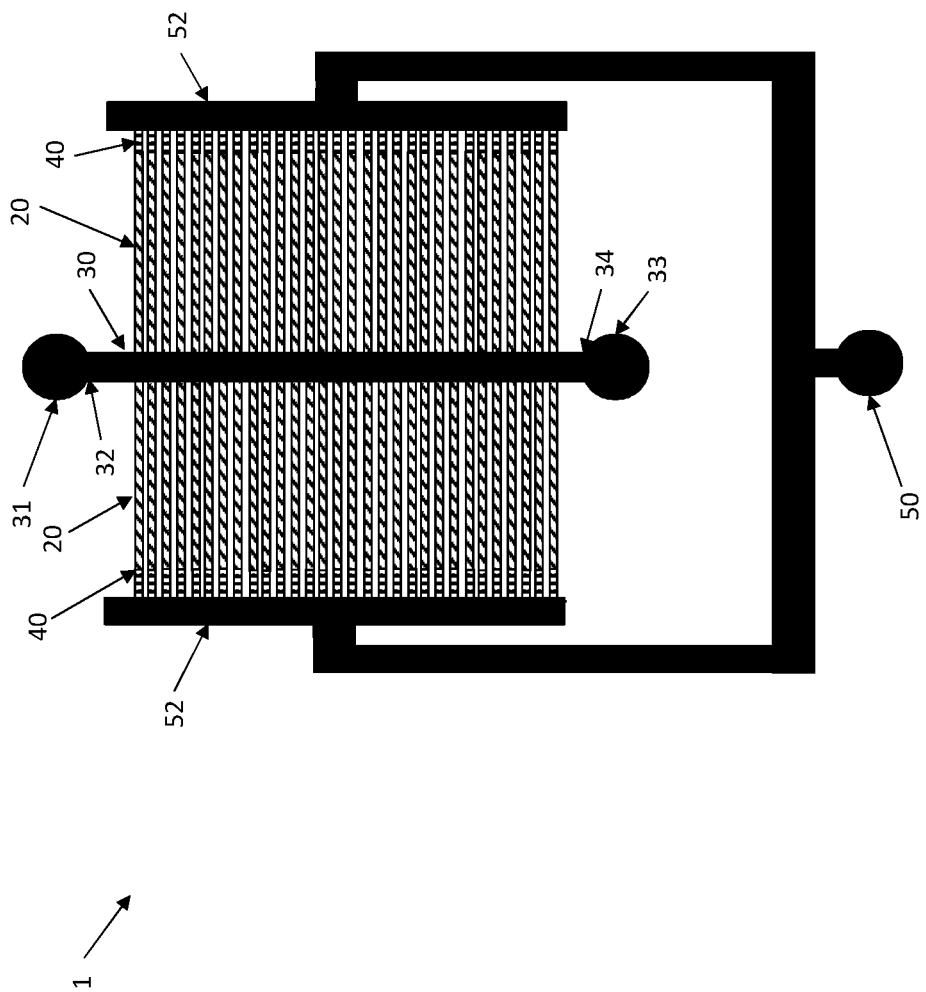
FIG. 6 is an illustration of a culturing device according to yet another embodiment.

The structure of cell channels 20 can be multiplexed, see for example FIGS. 6 and 7. The common feature being that cells are mechanically constricted to grow in a monolayer and that they are flooded with media, buffers, enzymes etc. without being washed away since they are physically too big to be pushed into the wash channels 40. It also requires two sinks for the cell channels, one to accommodate the excess cells that do not fit in a monolayer, i.e. the fluid sink 33, and one to accommodate the media that flows over the cells, i.e. the wash sink 50.

The microfluidic device 1 of FIG. 6 basically multiplexes two structures as shown in FIG. 5. This means that the two structures of cell channels 20 and wash channels 40 (left and right in the figure) share a common flow channel 30 connected in its first end 32 to the fluid source 31 and in its second end 34 to the fluid sink 33. Each structure of cell channels 20 and wash channels 20 ends at a respective sink channel 52 that are interconnected and connected to a common wash sink 50.

The cells present in cell channels 20 in the structure to the left will be exposed to the same culture medium and reagents and chemicals input at the fluid source 31 as the cells present in the cell channels in the structure to the right in the figure.

FIG. 7 illustrates an embodiment of a microfluidic device 1 having multiple, i.e. at least two, structures of cell channels 20 and wash channels 40 share a common fluid sink 33 and wash sink 50 but have separate, i.e. individual, fluid sources 31. This means that different culture medium and/or reagents or chemicals can be input to cells present in one of the structures of cells channels 20 as compared to cells present in another of the structures of cells channels 20.

During loading, cells and culture medium enters the fluid sink 33 with media flowing out through the wash sink 50 and the separate fluid sources 31, whereas excess cells flow out through the fluid sources 31. In another embodiment, the cells enter the individual fluid sources 31 with excess cells exiting the common fluid sink 33. During operation, media enter the separate fluid sources 31, thereby allowing different media to enter the different structures of cells channels 20 and wash channels 40. Excess cells are washed out through the fluid sink 33 and media flow out from the wash sink 50 and also out through the common fluid sink 33.

Figure 3:
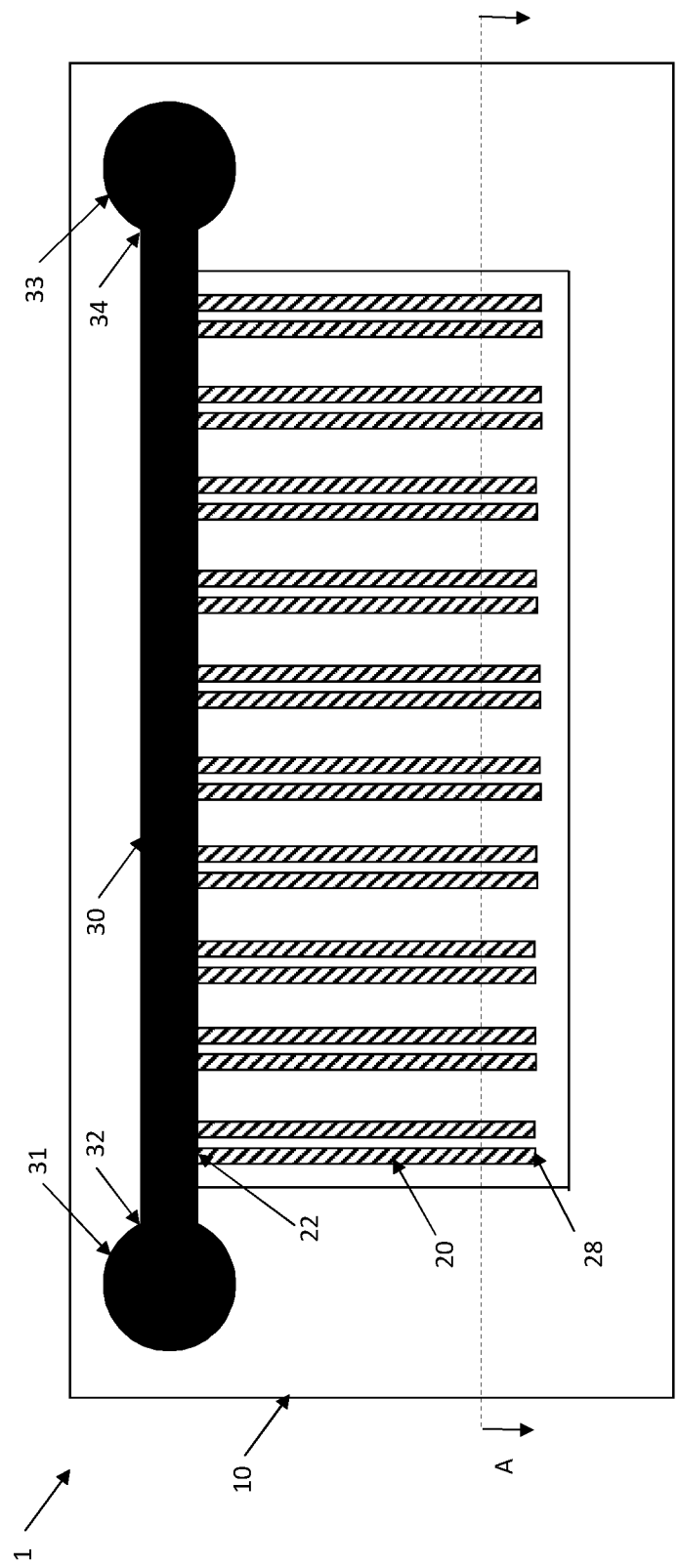
FIG. 3 is an illustration of a culturing device according to another embodiment.

FIGS. 3 and 4 illustrate another embodiment of the microfluidic device 1 that lacks wash channels, wash source and wash sink. In clear contrast, the microfluidic device 1 comprises a semipermeable membrane 80 having an average pore size that is smaller than an average diameter of the cells. The semipermeable membrane 80 is arranged on the substrate 10 to form a lid for the plurality of spatially defined and separated cell channels 20.

In this embodiment, the cell channels 20 are open channels having an opening in one of the main surfaces 12 of the substrate 10. The semipermeable barrier 80 is then positioned on this main surface 12 to form a lid for the cell channels 20.

During washing, the washing fluid or liquid may efficiently flow through the cell channels 20 from the fluid source 31 and flow channel 30 and out through semipermeable barrier 80. The average pore size of the semipermeable barrier 80 is selected to prevent the cells from passing through the semipermeable barrier 80 but allow the washing fluid or liquid to pass there through.

The substrate 10 may be made in any transparent material, such as plastic material, in which the structures constituting the cell channels 20, the fluid source 31, the fluid sink 33, the flow channel 30 and optionally the wash channels 40, sink channel 52 and wash sink 50 can be defined. Non-limiting examples of suitable materials include ZEONEX® and ZEONOR®, which are cyclic olefin polymers (COP) marketed by ZEON Chemicals L.P. and TOPAS®, which are cyclic olefin copolymers (COC) marketed by Topas Advanced Polymers. These materials have excellent optical characteristics in terms of transmission and background fluorescence. They also have good flow characteristics when heated and may therefore replicate small structures allowing formation of substrates 10 as shown in FIGS. 1-7.

Other examples of suitable materials for the substrate 10 include glasses, polydimethylsiloxane (PDMS), poly(methyl methacrylate) (PMMA), polycarbonate (PC), polypropylene (PP), polytetrafluoroethylene (PTFE), polyethylene terephthalate (PET) and poly(p-phenylene sulfide) (PPS).

The semipermeable membrane 80 can be selected among dialysis membranes, such as marketed by Thermo Fisher Scientific Inc. Alternatively, the semipermeable membrane 80 may be manufactured from any of the plastic materials mentioned above for the substrate 10.

The cover plate 70 may be manufactured in various materials that are preferably transparent to allow imaging. Non-limiting examples include glass and plastic materials.

In an embodiment, the system also comprises a fluidic manifold configured to distribute components of the first kit to the cell channels 20 using at least one computer-controlled pump. The fluidic manifold is preferably configured to enable change of media for phenotyping, distribution of chemicals used for cell fixation and apply needed for in situ sequencing using the computer-controlled and preprogramed pumps. In a particular embodiment, the reagents and cell culture media can be maintained at different temperatures throughout the experiment.

In an embodiment, each cell strain has a respective strain-specific barcode sequence in its genome or a mobile genetic element. The first kit then comprises components for determining the respective genotype by in situ sequencing at least a part of the respective specific barcode sequence of each cell strain at the spatially defined and separated positions in the culturing device.

The system of the embodiments may, for instance, be used for phenotyping and genotyping bacteria. In such a case, the cell channels 20 preferably have dimensions between 800-1200 nm and the wash channels 40 are preferably less than 400 nm high. In a particular embodiment, the microfluidic device 1 preferably comprises more than 1000 cell channels 20 that are advantageously individually marked and, thus, recognizable.

The microfluidic device 1 of the embodiments is highly suitable for usage in the system for characterizing a library of a plurality of cell strains. However, the microfluidic device 1 could alternatively be used for other purposes than allowing determination of both phenotype and genotype of a library of cell strains, such as screening for antibiotic resistance and other screening operations.

Hence, an aspect of the embodiments relates to a microfluidic device 1 comprising a substrate 10 transparent for imaging and having a plurality of spatially defined and separated cell channels having a dimension to accommodate cells in monolayer. A respective first end 22 of the plurality of spatially defined and separated cell channels 20 is in fluid connection with a flow channel 30 having a first end 32 in fluid connection with a fluid source 31 and a second end 34 in fluid connection with a fluid sink 33. A respective second end 28 of the plurality of spatially defined and separated cell channels 20 is in fluid connection with a first end 42 of a respective wash channel 40 having a second end 44 in fluid connection with a sink channel 52, which is in fluid connection with a wash sink 50. The wash channels 40 have a dimension too small to accommodate cells.

In an embodiment, each cell channel 20 is flanked along at least one of its longitudinal sides 24, 26 with a respective second wash channel 40 having a first end 42 in fluid connection with the flow channel 30 and a second end 44 in fluid connection with the wash channel 52.

In an embodiment, the first kit comprises components for in situ sequencing by ligation of the at least a part of the respective specific barcode sequence at the spatially defined and separated positions in the culturing device.

In this embodiment, the first kit preferably comprises a DNA ligase, an anchor primer having a nucleotide sequence that is complementary to the nucleotide sequence of a library-common primer-binding sequence in the genome of the cell strains, a mixed pool of labelled interrogation probe oligonucleotides. The first kit preferably also comprises a reaction mixture containing components required for the DNA ligase (ATP, buffer) to join a labelled probe oligonucleotide to the anchor primer base-pairing with the library-common primer-binding sequence and for cleaving the hybridized probe at uracil (uracil-DNA glycosylase).

In another embodiment, the first kit comprises components for in situ sequencing by synthesis of the at least a part of the respective specific barcode sequence at the spatially defined and separated positions in the culturing device.

In this embodiment, the first kit preferably comprises four types of modified dNTPs containing a reversible terminator that contains a fluorescent label. The first kit preferably also comprises a DNA polymerase and a sequencing primer having a nucleotide sequence that is complementary to the nucleotide sequence of a library-common primer-binding sequence in the genome of the cell strains. The first kit also comprises a reaction mixture containing components required for the DNA polymerase to incorporate the modified nucleotides to the sequencing primer.

The system preferably also comprises mapping information specifying a connection between each variable region and a respective strain-specific barcode sequence. The respective genotype is then determined based on the in situ sequenced at least a part of the respective strain-specific barcode sequence and the mapping information.

In an embodiment, each cell strain of the library has a respective construct comprising a respective strain-specific barcode sequence and the variable region in its genome flanked by library-common primer-binding sequences of known nucleotide sequence. The library-common primer-binding sequences can thereby be used to amplify the respective strain-specific barcode sequence from the genome or via a transcribed RNA sequence that is reverse transcribed into a cDNA sequence.

In an embodiment, the system comprises a second kit comprising components for synthesizing, for each cell strain, a cDNA sequence from a transcribed RNA sequence using primers complementary to at least one library-common primer-binding sequence in the transcribed RNA sequence and a reverse transcriptase or an RNA-dependent DNA polymerase. The first kit then preferably comprises components for in situ sequencing the at least part of the respective strain-specific barcode sequence in the cDNA sequence of each cell strain at the spatially defined and separated positions in the culturing device.

The second kit preferably comprises a primer sequence that is complementary to at least one library-common primer-binding sequence in the transcribed RNA sequence and the reverse transcriptase or RNA-dependent DNA polymerase. The second kit also comprises the nucleotides that are used by the enzyme to generate the cDNA sequence. The second kit also comprises a reaction mixture containing components required for the reverse transcriptase or RNA-dependent DNA polymerase to incorporate the nucleotides, such as the reverse transcriptase, dNTPs, RNAse inhibitors. The second kit preferably also comprises an RNase to degrade residual RNA following the reverse transcription.

In an embodiment, the system also comprises a third kit comprising components (DNA polymerases, ligase, dNTPs) for in situ amplifying the cDNA sequence by rolling circle amplification following circulation using ssDNA ligase or a padlock probe, or by in situ PCR.

In an embodiment, the system further comprises a fourth kit comprising components for fixating the cells at the spatially defined and separated positions in the culturing device. This fourth kit preferably comprises formaldehyde that can be used to fixate the cells.

The components of the kits in the system can be provided as separate components in dedicated containers. Alternatively, at least some of the components of a kit may be provided a as a mixture present in a same container.

The method and system of the embodiments can be used in various applications in where there is a need to phenotypically characterize a library of cell strains and associating the various phenotypes to the different genotypes in the library.

For instance, the embodiments can be used to optimize fluorescent proteins or RNA aptamers to select for fast maturing intracellular signals. In this application the protein or RNA-coding region of the reporter, i.e. a fluorescent protein or the apatmer, would be encoded in the variable region of the genome. The expression of the reporter may be induced by a chemical agent, such as isopropyl β-D-1-thiogalactopyranoside (IPTG) of the reporter is regulated the by the lac repressor protein. The culture media or cells also contain any cofactor that is needed for the reporter florescence. The phenotype is monitored by measuring fluorescence over time after induction and the phenotypes are scored by the time for reaching a specific level of fluorescence or the fluorescence that is reached after a specific time or the time constant for relaxation to the steady-state fluorescence value.

In an embodiment, the library of cell strains could be a library in which genes can be downregulated by a chemical signal, such as the expression of a guide RNA for dCAS9. The cell strains could then be barcoded with known mapping information between the barcode and the particular gene.

Furthermore, the embodiments can be used to identify gene regulatory RNA sequences or proteins by sensitive detection of regulator properties in vivo. Thus, the variable regions then encode different such gene regulatory RNA sequences or proteins. The regulatory effect of the RNA sequences or proteins can then be monitored, for instance by microscopy, in order to detect various phenotypic characteristics that are caused by the gene regulation.

The embodiments may also be used to select proteins or peptides for inhibition or activation of biological processes in the cells. The variable regions then encode different versions of the proteins or peptides. The phenotypic monitoring then involves monitoring for the inhibition or activation of the relevant biological process.

Furthermore, the variable regions in the cell strains of the library may be a set of expressed sequences that repress or enhance expression or regulation of specific genes. This can for example be interference RNA (iRNA) or short guied mRNA (sgRNA) sequences that can be constitutively expressed or conditional. The phenotypes can be screened for differences in phenotype, such as problems in development, growth, differentiation, and in their different responses to added test agents.

The embodiments can further be used to identify which genes that are required in specific steps in differentiation cells, such as stem cells, or in responses to a test agent. The variable regions may encode different sgRNA or iRNA that repress expression of different genes, such that different gene are effectively shut off in different cells. The phenotypic characterization may be in the form of monitoring the differentiation of cells in response to chemical test agents, such as growth factors or a drug. If cells, tissues or organisms display an alteration in some steps of differentiation, the gene that has altered expression in that cell strain is related to the alerted differentiation. Using a very similar approach, it is possible to study and determine the genes that are important for development in multicellular organisms or tissues or proliferation of cancer cells.

It is also possible to screen for regulatory sequences that respond to a specific stimuli by monitoring reporter protein expression with a multitude of regulatory sequences. Hence, the variable regions then correspond to the regulatory sequences. The phenotypic determination is then based on monitoring reporter protein expression in the cells and where the gene encoding the reporter gene is under regulatory control of the regulatory sequences. The cells are then exposed to specific stimuli, such as physical stimuli, e.g. temperature changes, or chemical stimuli, e.g. addition of test agent, and the response thereto is monitored through the reporter gene expression.

The method and system of the embodiments can be used to identify interaction partners and regulators of a gene or gene product by monitoring the localization, diffusion or concentration of the gene or gene product in a library where other gene products are selectively and conditionally knocked down. In this case, the variable regions may encode different products that achieve the selective and conditional knock down, for instance iRNA and sgRNA. In a similar application, one can use a knock down library in combination with phenotypic monitoring of a fluorescently tagged protein of interest in order to study its intracellular diffusion, localization or concentration. The library screen could in this case directly identify potential interaction partners or regulators.

A barcoded genomic mutation library can be made in parallel by introducing three elements to a cell, for example by having them in the same plasmid. The three elements include (1) a homologues but partially mutated DNA sequence corresponding to the desired introduced change (variable region), (2) a guide RNA for CRISPR-mediated DNA cleavage of the corresponding unmutated DNA sequences and (3) a barcode sequence for in situ sequencing. The barcode sequence can be maintained on a mobile genetic element or be introduced at a separate position on the chromosome.

When it is possible to monitor the biosynthesis of a compound of interest in the microscope or by a biosensor integrated in the culturing device this can be used as phenotypic readout to optimize expression levels for enzymes in a biosynthesis pathway or their amino acid sequences.

The above described applications should merely be seen as a few but illustrative uses of the method and system of the embodiments.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method of characterizing a library of a plurality of cell strains having different variable regions in at least one part of the genetic material of said cell strains, said method comprising:
   loading cells of said cell strains with media into a fluid source of a microfluidic device comprising a substrate having a plurality of spatially defined and separated cell channels configured to accommodate cells, wherein respective first ends of said plurality of spatially defined and separated cell channels are in fluid connection with a flow channel having said fluid source at a first end of said flow channel and a fluid sink at a second end of said flow channel, wherein respective second ends of said plurality of spatially defined and separated cell channels are in fluid connection with first ends of respective wash channels having second ends in fluid connection with a sink channel that is in fluid connection with a wash sink, wherein said wash channels have a dimension too small to accommodate cells;
   culturing cells of said cell strains at said spatially defined and separated cell channels in said microfluidic device;
   determining a phenotypic characteristic of each cell strain in said spatially defined and separated cell channels in said microfluidic device;
   fixating said cells of said cell strains at said spatially defined and separated cell channels in said microfluidic device;
   in situ genotyping said variable region of each cell strain at said spatially defined and separated cell channels in said microfluidic device; and
   connecting each respective phenotypic characteristic to each respective genotype based on said spatially defined and separated cell channels in said microfluidic device.

2. The method according to claim 1, wherein in situ genotyping comprises in situ sequencing by ligation of said variable region or at least a portion thereof at said spatially defined and separated cell channels in said microfluidic device.

3. The method according to claim 1, wherein in situ genotyping comprises in situ sequencing by synthesis of said variable region or at least a portion thereof at said spatially defined and separated cell channels in said microfluidic device.

4. The method according to claim 1, wherein each cell strain has a respective strain-specific barcode sequence in its genetic material and in situ genotyping comprises determining said respective genotype by in situ sequencing at least a part of said respective strain-specific barcode sequence of each cell strain at said spatially defined and separated cell channels in said microfluidic device.

5. The method according to claim 4, further comprising:
   determining mapping information specifying a connection between each variable region and a respective strain-specific barcode sequence, wherein determining said respective genotype comprises determining said respective genotype based on said in situ sequenced at least a part of said respective strain-specific barcode sequence and said mapping information.

6. The method according to claim 5, wherein determining said mapping information comprises sequencing said library of cell strains in bulk to obtain, for each cell strain, a sequence read encompassing said variable region and said respective strain-specific barcode sequence.

7. The method according to claim 4, wherein each cell strain has a respective construct comprising a respective strain-specific barcode sequence and said variable region in its genetic material flanked by at least one library-common primer-binding sequence of known nucleotide sequences that can be used to amplify said respective strain-specific barcode sequence or sequence said respective strain-specific barcode sequence from said genetic material or via a transcribed ribonucleic acid, RNA, sequence that is reverse transcribed into a complementary deoxyribonucleic acid, cDNA, sequence.

8. The method according to claim 7, further comprising synthesizing, for each cell strain, a cDNA sequence from a transcribed RNA sequence using primers complementary to at least one library-common primer-binding sequence in said transcribed RNA sequence and a reverse transcriptase or an RNA-dependent DNA polymerase, wherein in situ sequencing comprises in situ sequencing said at least part of said respective strain-specific barcode sequence in said cDNA sequence of each cell strain at said spatially defined and separated cell channels in said microfluidic device.

9. The method according to claim 7, further comprising in situ amplifying said cDNA sequences by rolling circle amplification following circulation using single-stranded DNA, ssDNA, ligase or a padlock probe or by in situ polymerase chain reaction, PCR, or by ligating said cDNA sequences after self-hybridization.

10. The method according to claim 7, further comprising in situ amplifying said respective strain-specific barcode sequence or in situ sequence said respective strain-specific barcode sequence from said genetic material by rolling circle amplification following excision of said respective strain-specific barcode sequence from said genetic material.

11. The method according to claim 4, wherein in situ sequencing comprises in situ sequencing by ligation of said at least a part of said respective strain-specific barcode sequence at said spatially defined and separated cell channels in said microfluidic device.

12. The method according to claim 4, wherein in situ sequencing comprises in situ sequencing by synthesis of said at least a part of said respective strain-specific barcode sequence at said spatially defined and separated cell channels in said microfluidic device.

13. The method according to claim 1, wherein determining said phenotypic characteristic comprises determining said phenotypic characteristic of each cell strain during culturing of said cells in said microfluidic device using microscopy.

14. The method according to claim 1, further comprising adding at least one test agent to said cells in said culturing device, wherein determining said phenotypic characteristic comprises determining a phenotypic response of each cell strain to said at least one test agent in said microfluidic device.

15. The method according to claim 1, further comprising randomly seeding cells of said cell strains at said spatially defined and separated cell channels in said microfluidic device so that each spatially defined and separated position only comprises cells of a same genotype.

16. A system for characterizing a library of a plurality of cell strains having different variable regions in at least one part of the genetic material of said cell strains, said system comprises:
a microfluidic device configured to culture cells of said cell strains at spatially defined and separated cell channels in said microfluidic device, wherein said microfluidic device comprises a substrate having a plurality of spatially defined and separated cell channels configured to accommodate cells, wherein respective first ends of said plurality of spatially defined and separated cell channels are in fluid connection with a flow channel having a fluid source at a first end of said flow channel and a fluid sink at a second end of said flow channel, wherein respective second ends of said plurality of spatially defined and separated cell channels are in fluid connection with first ends of respective wash channels having second ends in fluid connection with a sink channel that is in fluid connection with a wash sink, wherein said wash channels have a dimension too small to accommodate cells;
a first kit comprising components for fixating said cells at said spatially defined and separated cell channels in said microfluidic device; and
a second kit comprising components for in situ genotyping said variable region of each cell strain following fixation of said cells at said spatially defined and separated cell channels in said microfluidic device, wherein a respective phenotypic characteristic of each cell strain can be connected to each respective genotype based on said spatially defined and separated cell channels in said microfluidic device.

17. The system according to claim 16, further comprising a microscope arranged for determining a phenotypic characteristic and a genotype of each cell strain in said spatially defined and separated cell channels in said microfluidic device.

18. The system according to claim 16, further comprising said library of said plurality of cell strains.

19. The system according to claim 16, wherein said substrate is transparent for imaging.

20. The system according to claim 19, wherein each cell channel is flanked along at least one of its longitudinal sides with a respective second wash channel having a first end in fluid connection with said flow channel and a second, opposite end in fluid connection with said sink channel, said second wash channels having a dimension that is too small to accommodate cells.

21. The system according to claim 19, further comprising a fluidic manifold configured to distribute said components of said first kit to said cell channels using at least one computer-controlled pump.

22. The system according to claim 16, wherein each cell strain has a respective strain-specific barcode sequence in its genetic material and said second kit comprises components for determining said respective genotype by in situ sequencing at least a part of said respective strain-specific barcode sequence of each cell strain at said spatially defined and separated cell channels in said microfluidic device.

23. The system according to claim 22, further comprising mapping information specifying a connection between each variable region and a respective strain-specific barcode sequence, wherein said respective genotype is determined based on said in situ sequenced at least a part of said respective strain-specific barcode sequence and said mapping information.

24. The system according to claim 22, wherein each cell strain has a respective construct comprising a respective strain-specific barcode sequence and said variable region in its genetic material flanked by at least one library-common sequence of known nucleotide sequences that can be used to amplify said respective strain-specific barcode sequence or sequence said respective strain-specific barcode sequence from said genetic material or via a transcribed ribonucleic acid, RNA, sequence that is reverse transcribed into a complementary deoxyribonucleic acid, cDNA, sequence.

25. The system according to claim 24, further comprising a third kit comprising components for synthesizing, for each cell strain, a cDNA sequence from a transcribed RNA sequence using primers complementary to at least one library-common primer-binding sequence in said transcribed RNA sequence and a reverse transcriptase or an RNA-dependent DNA polymerase, wherein said second kit comprises components for in situ sequencing said at least part of said respective strain-specific barcode sequence in said cDNA sequence of each cell strain at said spatially defined and separated cell channels in said microfluidic device.

26. The system according to claim 24, further comprising a fourth kit comprising components for in situ amplifying said cDNA sequences by rolling circle amplification following circulation using single-stranded DNA, ssDNA, ligase or a padlock probe or by in situ polymerase chain reaction, PCR, or by ligating said cDNA sequence after self-hybridization.

27. The system according to claim 22, wherein said second kit comprises components for in situ sequencing by ligation of said at least a part of said respective strain-specific barcode sequence at said spatially defined and separated cell channels in said microfluidic device.

28. The system according to claim 22, wherein said second kit comprises components for in situ sequencing by synthesis of said at least a part of said respective strain-specific barcode sequence at said spatially defined and separated cell channels in said microfluidic device.

* * * * *

UNITED STATES PATENT AND TRADEMARK OFFICE
CERTIFICATE OF CORRECTION

PATENT NO. : 10,570,437 B2  
APPLICATION NO. : 15/323352  
DATED : February 25, 2020  
INVENTOR(S) : Elf et al.

Page 1 of 1

It is certified that error appears in the above-identified patent and that said Letters Patent is hereby corrected as shown below:

On the Title Page

Item (30), change "1450860" to --1450860-0--.

Signed and Sealed this  
Seventh Day of April, 2020

Andrei Iancu  
*Director of the United States Patent and Trademark Office*